United States Patent [19]

Gutierrez et al.

[11] Patent Number: 4,850,866
[45] Date of Patent: Jul. 25, 1989

[54] METHOD AND APPARATUS FOR MEASURING THE LENGTH OF THE ROOT CANAL OF A TOOTH

[76] Inventors: Alberto Gutierrez; Carlos Gutierrez, both of P.O. Box 52660, Bogota D.E., Colombia

[21] Appl. No.: 202,487

[22] Filed: Jun. 6, 1988

[51] Int. Cl.⁴ ............................................. A61C 19/04
[52] U.S. Cl. ........................................ 433/72; 128/776
[58] Field of Search .................... 433/72; 128/734, 736

[56] References Cited
U.S. PATENT DOCUMENTS 3,753,434  8/1973  Pike et al. .............................. 433/72
3,916,529  11/1975  Mousseau ............................... 433/72

Primary Examiner—Robert Peshock
Attorney, Agent, or Firm—Norman B. Rainer

[57] ABSTRACT

A method and apparatus are provided for use by dentists in determining the actual length of a root canal based upon a single x-ray picture. The method involves inserting a probe a known distance partially into the root canal before taking the x-ray picture. The picture is then analyzed to compare the visually observed, apparent lengths of the root canal and probe with the known length of the probe. The actual length of the root canal is determined by direct arithmetic proportion based upon the observed apparent lengths. The apparatus facilitates measurement of said observed apparent lengths utilizing manipulating knobs and an illuminated scale resembling a thermometer scale.

10 Claims, 3 Drawing Sheets

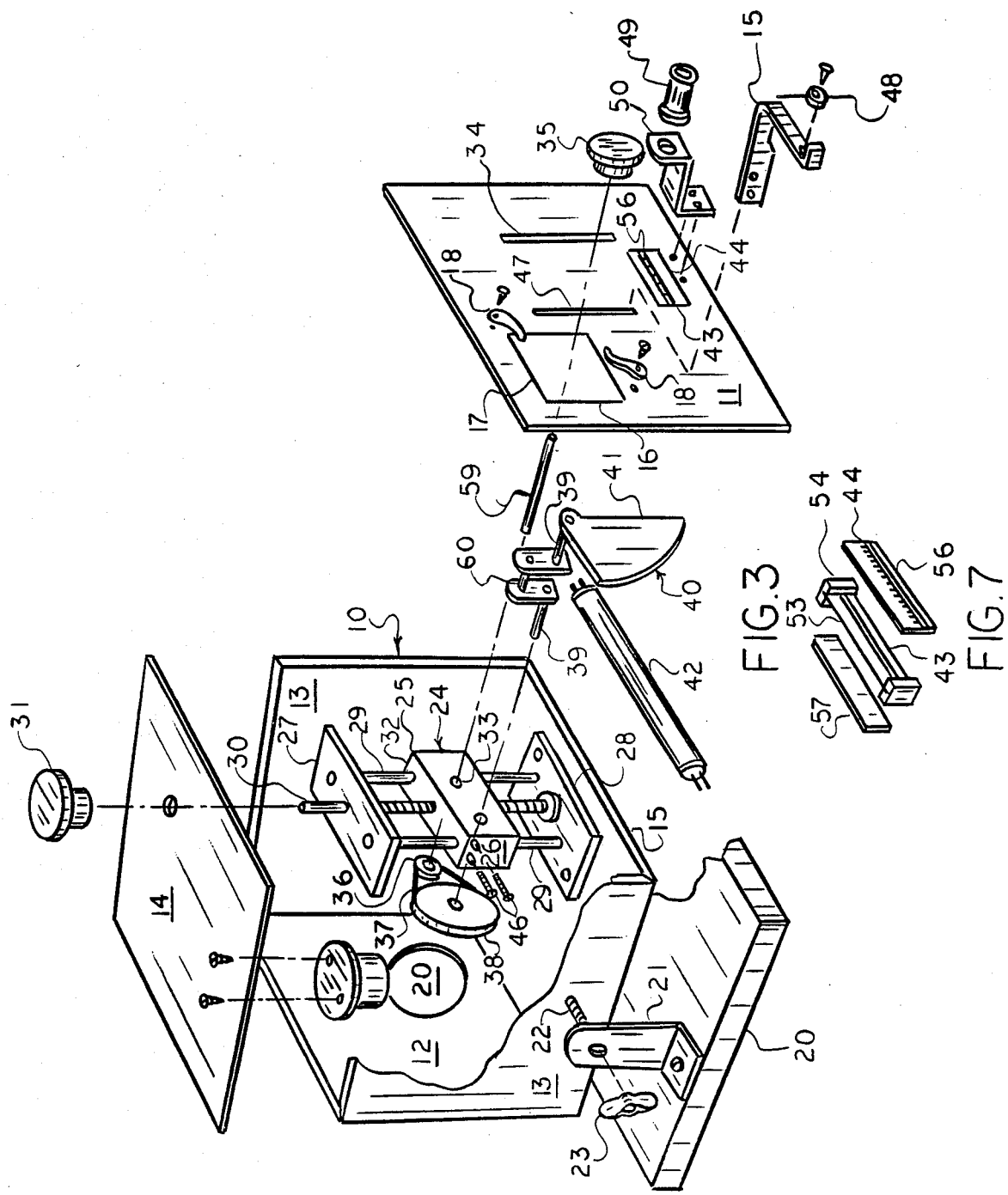

METHOD AND APPARATUS FOR MEASURING THE LENGTH OF THE ROOT CANAL OF A TOOTH

BACKGROUND OF THE INVENTION

This invention relates to a dental procedure for determining the length of the root canal of a tooth of a patient, and apparatus for use in said procedure.

In the dental treatment of a decayed tooth, it is often necessary for the dentist to known the exact length of the root canal, such length sometimes being referred to as the endodontic working length. Endodontic treatments usually involve drilling a hole through the crown of the tooth to gain access to the underlying root canal. The pulp within the canal is then removed by use of fine diameter reamers and files. The cleaning of the canal is generally referred to as biomechanical preparation; and thoroughness of such cleaning is essential for disinfection purposes and filling the canal. Prior to the preparation of the canal, the dentist must determine the exact canal length to prevent the touching or penetration of the periapical tissues by the cleaning instruments with attendant inflammation or infection.

The most commonly employed technique for measuring the endodontic working length is by inserting a metal probe into the root canal in incremental steps while taking x-ray pictures to determine the degree of penetration of the probe. Such technique exposes the patient to considerable x-ray dosage, and still risks contact with the periapical tissues or periodontal membrane of the apex of the canal.

More recently, electronic devices have been utilized wherein electrical signals emitted from an electrode inserted into the canal to a depth close to the apex are modulated by the chemical and physical characteristics of the canal. The magnitude of the modulated signal is indicative of the length of the canal. However, variable amounts of water, blood or exudate within the canal, and the presence of lateral foramina or perforations cause measurements by electronic devices to be unreliable. Also, the probe may push material within the canal against the apical area, thereby producing irritation.

Although the total apparent length of the root canal can be seen on an x-ray picture, the true length is not determinable from the x-ray picture because of the unknown orientation of the tooth with respect to the plane of the x-ray film.

It is accordingly an object of the present invention to provide a method for accurately and reliably determining endodontic working length without subjecting the patient to repeated x-ray exposure, and without risk of contacting the periapical tissue.

It is a further object of this invention to provide apparatus useful in the method of the foregoing object.

It is another object of the present invention to provide apparatus of the aforesaid nature of simple construction and amenable to easy operation by the dentist.

These objects and other objects and advantages of the invention will be apparent from the following description.

SUMMARY OF THE INVENTION

The above and other beneficial objects and advantages are accomplished in accordance with the present invention by a method for determining the true total length of a root canal comprising: (a) inserting a known length of a probe into the canal, said length being substantially less than the true total length of the canal and considered a true partial length thereof, (b) making an x-ray picture (a radiograph) of the tooth containing said probe, said radiograph showing the tooth canal as an apparent total length and showing the probe as an apparent partial length, and (c) determining the true total length of the canal using an apparatus in which mechanical means are caused to travel the apparent partial and total lengths, and provide a read-out of the true total length based upon a proportionality determined by the ratio of the true partial length to the apparent partial length.

The apparatus of this invention is comprised of:
(a) a box-like enclosure having vertically disposed front, rear, and side panels, and horizontally disposed top and bottom panels,
(b) an aperture disposed within said front panel, and means associated therewith to hold a radiograph,
(c) an electric light source positioned within the enclosure in a manner to direct light through said aperture,
(d) a holding block positioned within the enclosure and adapted to move vertically therein by threaded control means, said holding block being elongated between first and second lateral extremities,
(e) a horizontally disposed control rod rotatably held by said block adjacent said first lateral extremity and having a rear extremity rearwardly displaced from said block, and a forward extremity disposed forwardly of said front panel, said control rod passing through a first vertical slot in said front panel,
(f) pulley means associated with the rear extremity of said control rod and adapted to transfer turning force to a driven shaft rotatively held by said block in parallel disposition to said control rod, said driven shaft having a forward extremity disposed between said block and front panel,
(g) an obscuring plate attached to the forward extremity of said driven shaft and having a downwardly directed straight edge, said obscuring plate being rotatable by said shaft in a plane parallel to said front panel,
(h) a horizontally disposed fluorescent bulb positioned between said block and obscuring plate,
(i) a horizontally disposed slot disposed in said front panel adjacent said fluorescent bulb and having a window provided with a ruler-type linear scale of distance markings, said horizontally disposed slot being located so as to be traversed by the straight edge of said obscuring plate,
(j) an extension arm attached to said block adjacent said second lateral extremity and forwardly directed through a second vertical slot in said front panel, terminating in a forward extremity, and
(k) an upwardly directed pointer attached to the forward extremity of said extension arm and positioned beneath the midpont of said aperture.

In preferred embodiments of the invention, light shielding means are associated with the two vertical slots in the front panel to prevent the emergence of light from the enclosure. Knobs may be associated with the threaded control means and control rod exterior to the enclosure to facilitate manual rotation of said control means and control rod. An optical viewing device may be positioned in front of the horizontal slot to facilitate accurate reading of the distance scale. The enclosure may be pivotably mounted to expedite positioning at a convenient angle above a work surface.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing:

FIG. 3 is an exploded perspective view of the embodiment of FIG. 2.

FIG. 7 is a partially exploded perspective view of an embodiment of a slit assembly component of this invention.

DESCRIPTION OF THE PREFERRED EMBODIMENT

Figure 2:
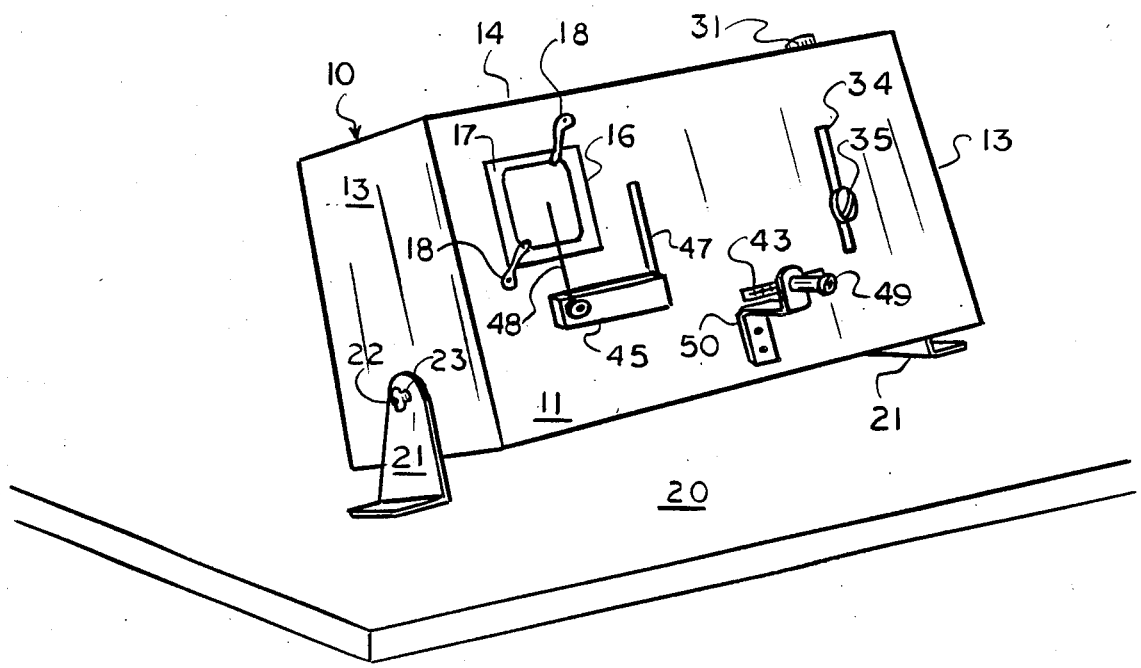
FIG. 2 is a perspective front view of an embodiment of the apparatus of this invention.
Figure 1:
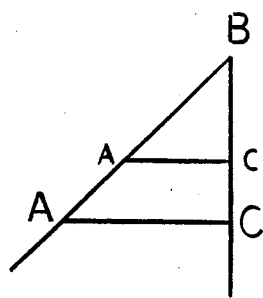
FIG. 1 is a schematic representation of fundamental principles underlying the method and apparatus of this invention.

Referring to FIG. 1, two triangles are shown having the common vertex B, and the parallel base lines ac and AC. By the well known laws of trigonometry:

$$(AC)/BS = (ac)/bc$$

If it is assumed that ac=partial true length, Bc=partial apparent length, and BC=total apparent length, then AC=total true length. Accordingly, by knowing the partial true length, namely the length of the probe, the partial apparent length, namely the length of the image of the probe on the radiograph, and the total apparent length, namely the length of the image of the root canal on the radiograph, the total true length of the root canal can be ascertained.

Referring to FIGS. 2-5, an embodiment of the apparatus of this invention is shown comprised of enclosure box 10 having vertically disposed front and rear panels 11 and 12, respectively, vertically disposed side panels 13, and horizontally disposed top and bottom panels 14 and 15 respectively. Said panels, preferably of sheet metal stock, are joined in a rectangular box configuration.

The enclosure box is supported above a platform base or table 20 by paired bracket arms 21 which pivotably engage bolts 22 extending outwardly from side panels 13. A wing nut 23 threadably engages each bolt 22, thereby enabling the box to be securely held in any pivoted position with respect to base 20.

A rectangular aperture 16 is disposed in front panel 11, said aperture confining a translucent window 17. Spring clips 18 are disposed about said window for the purpose of removably holding a radiograph upon said window. An electric light bulb 20, attached to the underside of top panel 14, illuminates window 17.

A holding block 24, elongated between first and second lateral extremities 25 and 26, respectively, is adapted to move in a vertical path within a frame structure comprised of upper plate 27, spaced apart parallel lower plate 28 affixed to bottom panel 15, and paired guide rods 29 extending vertically between said upper and lower plates. A vertical threaded rod 30 penetrates top panel 14 and upper plate 27, and engages a threaded vertical bore in block 24. The lowermost extremity of rod 30 is journaled to lower plate 28. The uppermost extremity of rod 30 is provided with turning knob 31. The guide rods 29 penetrate perpendicular smooth bores 32 within block 24. By turning rod 30, block 24 is caused to be raised or lowered while maintaining constant parallel alignment with front panel 11 by virtue of its sliding engagement with guide rods 29.

A horizontally disposed control rod 59 is rotatably held by smooth horizontal bore 33 in block 24 adjacent the first extremity thereof. The rear extremity of control rod 59 is rearwardly displaced from block 24. The forward portion of control rod 59 passes through first vertical slot 34 in front panel 11, and the forward extremity of said control rod being located forwardly of front panel 11 and equipped with turning knob 35.

Small pulley wheel 36 affixed to the rear extremity of control rod 59 interacts by way of resilient belt 37 with large pulley wheel 38 affixed to the rear extremity of driven shaft 39 rotatively held by block 24 in parallel disposition to control rod 59.

An obscuring plate 40, having downwardly directed straight edge 41, is affixed to the forward extremity of driven shaft 39 in a manner to be rotated by said shaft in a plane parallel to front panel 11.

A horizontally disposed fluorescent bulb 42 is positioned between block 24 and the obscuring plate. Electrical supply means of conventional nature, and accordingly not illustrated, is disposed within the box for energizing the fluorescent bulb and light bulb 20. In order to accommodate the flourescent bulb, driven shaft 39 is segmented, having an off-set portion 60.

A horizontally oriented slit 43 is disposed within front panel 11 adjacent said flourescent bulb, and positioned so as to be traversed by straight edge 41. The slit is provided with a window 44 having a ruler-type linear scale of distance markings 56. A preferred embodiment of a slit 43 and associated components is shown in FIG. 7 wherein slit 43 is formed by two steel blades 53 whose straight edges are held in spaced apart coplanar relationship by end blocks 54. The slit thereby formed is of .001 inch uniform width. A thin transparent red window 44 having a linear ruler scale of markings 56 is disposed forwardly of the slit. A second transparent red window 57 may be applied to the rear of slit 43.

An extension arm 45, attached by bolts 46 to the second lateral extremity of block 24 extends forwardly through a second vertical slot 47 in front panel 11, and terminates in a forward extremity which supports upwardly directed pointer 48 located beneath the midpoint of aperture 16. Pointer 48 is removably associated with extension arm 45 by virtue of a spring, threaded bolt, magnet, or other securing means, thereby enabling removal of the pointer to facilitate cleaning of window 17.

A viewing lens 49 is supported by bracket 50 in front of slit 43 to facilitate accurate parallax-free observation of scale 56.

Figure 6:
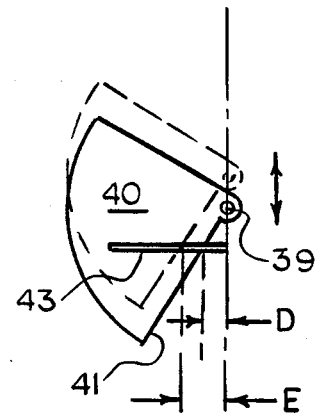
FIG. 6 is a schematic representation of apparatus factors affecting the principles depicted in FIG. 1.
Figure 5:
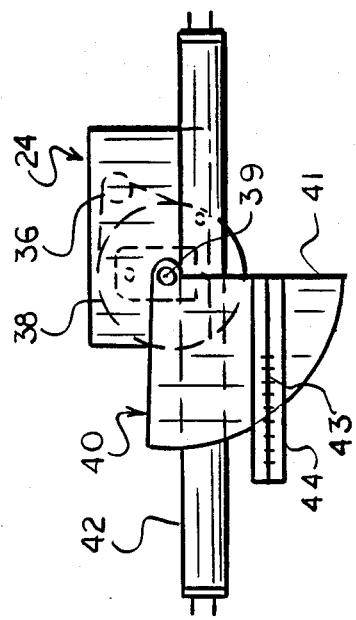
FIG. 5 is a fragmentary front view exemplifying the functional interactions of selected components.
Figure 4:
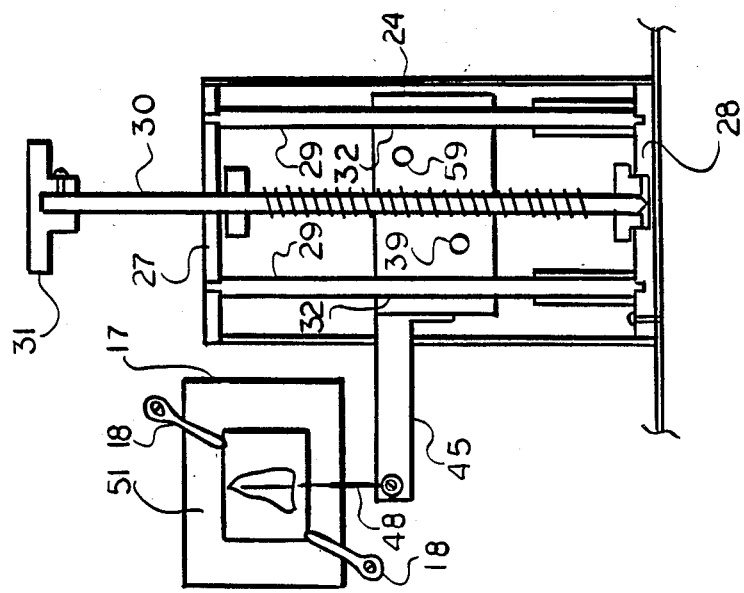
FIG. 4 is a schematic side view exemplifying the mode of operation of the embodiment of FIG. 2.

In the operation of the apparatus, a radiograph 51, shown in FIG. 4 is placed upon window 17 and held in place thereupon by spring holders 18. Knob 31 is turned so as to place block 24 in its lowest position. In such lowest position, the axis of driven shaft 39 intersects slit 43 at the extreme right or zero point of scale 56. The radiograph is adjusted in its position so that the tip of pointer 48 coincides with the beginning of the root canal, and said root canal is linearly aligned with the pointer. Knob 31 is then turned to elevate the tip until it coincides with the end of the end of the probe shown on the radiograph. Knob 35 is then rotated so that straight edge 41 is set, as shown in Figure 6, at a reading D on scale 56 that corresponds to the known true length of the probe. Such action illuminates scale 56 up to the location of straight edge 41. Then knob 31 is turned until the tip of the pointer coincides with the image of the apex of the root canal shown on the radiogram. At this point, the true length of the root canal is indicated by the illuminated length E on scale 56.

It should be noted, particularly by reference to FIG. 6, that the axis of driven shaft 39 corresponds to the vertex B of the triangles shown in FIG. 1. Similarly, the setting of the reading on scale 56 to correspond to the partial true length of the canal (or the known total inserted length of the probe, length (D) corresponds to line ac. The final reading E on scale 56 corresponds to line AC of the triangles of FIG. 1. The reading on scale 56 has the appearance of the well known red column of an alcohol-based thermometer.

While particular examples of the present invention have been shown and described, it is apparent that changes and modifications may be made therein without departing from the invention in its broadest aspect. The aim of the appended claims, therefore, is to cover all such changes and modifications as fall within the true spirit and scope of the invention.

Having thus described our invention, what is claimed is:

1. Apparatus for determining the true total length of a root canal comprising:
   (a) a box-like enclosure having vertically disposed front, bottom panels,
   (b) an aperture disposed within said front panel, and means associated therewith to hold a radiograph,
   (c) an electric light source positioned within the enclosure in a manner to direct light through said aperture,
   (d) a holding block positioned within the enclosure and adapted to move vertically therein by threaded control means, said holding block being elongated between first and second lateral extremities,
   (e) a horizontally disposed cotnrol rod rotatably held by said block adjacent said first lateral extremity and having a rear extremity rearwardly displaced from said block, and a forward extremity disposed forwardly of said front panel, said control rod passing through a first vertical slot in said front panel,
   (f) pulley means associated with the rear extremity of said control rod and adapted to transfer turning force to a driven shaft rotatively held by said block in parallel disposition to said control rod, said driven shaft having a forward extremity disposed between said block and front panel,
   (g) an obscuring plate attached to the forward extremity of said driven shaft and having a downwardly directed straight edge, said obscuring plate being rotatable by said shaft in a plane parallel to said front panel,
   (h) a horizontally disposed fluorescent bulb positioned between said block and obscuring plate,
   (i) a horizontally disposed slot disposed in said front panel adjacent said fluorescent bulb and having a window provided with a ruler-type linear scale of distance markings, said horizontally disposed slot being located so as to be traversed by the straight edge of said obscuring plate,
   (j) an extension arm attached to said block adjacent said second lateral extremity and forwardly directed through a second vertical slot in said front panel, terminating in a forward extremity, and
   (k) an upwardly directed pointer attached to the forward extremity of said extension arm and positioned beneath said aperture.

2. The apparatus of claim 1 wherein a light-transmitting flat window is disposed within said aperture substantially within the plane of said front panel.

3. The apparatus of claim 2 wherein spring clamps are associated with said flat window and adatped to hold thereupon an X-ray picture.

4. The apparatus of claim 1 wherein said driven shaft is segmented, having an off-set portion adapted to accommodate said fluorescent bulb.

5. The apparatus of claim 1 wherein the forward extremity of said extension arm is disposed in front of said front panel and parallel thereto.

6. The apparatus of claim 1 wherein said first and second vertical slots are in parallel alignment.

7. The apparatus of claim 1 wherein said pointer is removably associated with said extension arm.

8. The apparatus of claim 1 wherein an optical viewing device is positioned in front of said horizontal slot to facilitate accurate reading of said distance scale.

9. The apparatus of claim 1 wherein bracket arms pivotably engage the side panels of said enclosure.

10. A method for determining the true total length of a root canal comprising: (a) inserting a known length of a probe into the canal, said length being substantially less than the true total length of the canal and considered a true partial length thereof, (b) making an x-ray picture of the tooth containing said probe, said picture showing the tooth canal as an apparent total length and showing the probe as an apparent partial length, and (c) determining the true total length of the canal using an apparatus in which mechanical means are caused to travel the apparent partial and total lengths, and provide a read-out of the true total length based upon a proportionality determined by the ratio of the true partial length to the apparent partial length.

* * * * *